United States Patent [19]
Shindel

[11] Patent Number: 5,195,530
[45] Date of Patent: Mar. 23, 1993

[54] APPARATUS FOR ANALYZING EEG AND RELATED WAVEFORMS

[76] Inventor: Larry Shindel, 248 Rolling Hills Pl., Lancaster, Tex. 75146

[21] Appl. No.: 624,897

[22] Filed: Dec. 10, 1990

[51] Int. Cl.$^5$ .......................................... A61B 5/0476
[52] U.S. Cl. ................................................. 128/731
[58] Field of Search .................. 128/731; 364/413.05

[56] References Cited

U.S. PATENT DOCUMENTS

| | | | |
|---|---|---|---|
| 4,092,981 | 6/1978 | Ertl | 128/731 |
| 4,214,591 | 7/1980 | Sato et al. | 128/731 |
| 4,421,121 | 12/1983 | Whisler et al. | 128/731 |
| 4,736,751 | 4/1988 | Gevins et al. | 128/731 |

*Primary Examiner*—William E. Kamm
*Attorney, Agent, or Firm*—Strasburger & Price

[57] ABSTRACT

A method and apparatus for analyzing brain waves wherein the brain wave of interest is sampled, parameters that describe the brain wave are determined, and the parameters so determined are compared with standard parameters.

8 Claims, 8 Drawing Sheets

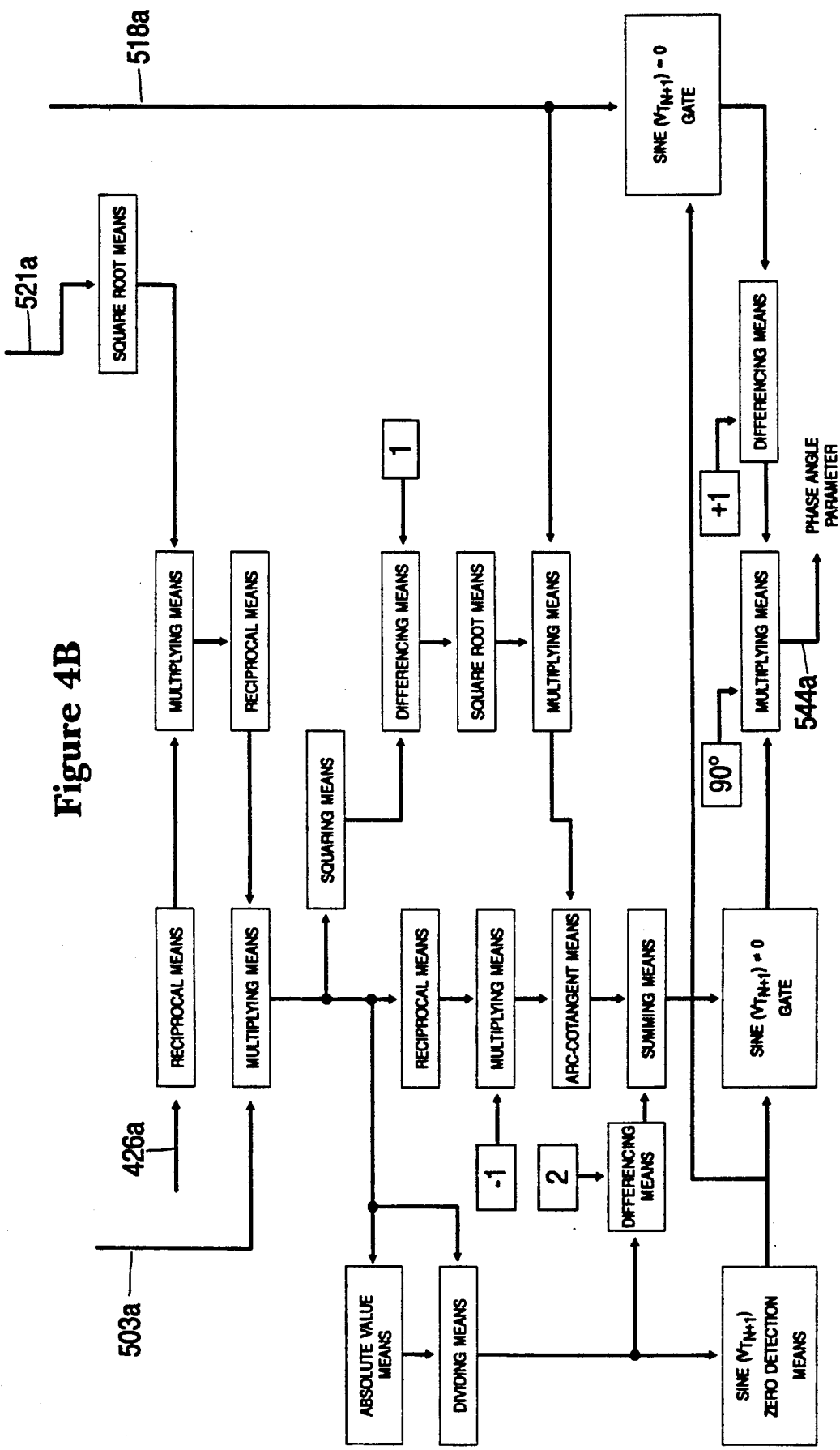

APPARATUS FOR ANALYZING EEG AND RELATED WAVEFORMS

FIELD OF THE INVENTION

This invention relates to apparatus for analyzing EEG and relating waveforms and in particular to such apparatus for deriving various parameters relating to such waveforms.

DISCUSSION OF THE PRIOR ART

The prior art reveals several related references as follows:

a. Peterson U.S. Pat. No. 2,313,666 entitled "Logarithmic Instrument Circuit" discloses a method comprising the steps of storing a charge, dissipating such charge, storing a second charge, and controlling a current;

b. Shaffer U.S. pat. No. 3,634,668 entitled "Log Spectrum Decoding Utilizing Symmetry" discloses a signal processor apparatus comprising function storage means, addressable locations, selecting means, multiplying means, storage means, a first input port, a second input port, a predetermined number of storage locations, function generator means, a common juncture, and accumulating means;

c. Blaess U.S. Pat. No. 4,275,446 entitled "Method And Apparatus for Measurement Of Attenuation And Distortion By A Test Object" discloses such a method comprising the steps of applying a test pulse and evaluating by Fourier analysis the deformation of such test pulse.

It is apparent from the above and the following that the above cited prior art references do not disclose the apparatus of the present invention.

INTRODUCTION

At present, the graphs of brain waves, obtained by means of an electroencephalograph (EEG), must be analyzed by an experienced, skilled technician. This is a very labor-intensive process and is subject to inevitable human error and diversity of opinion. An automated system of EEG analysis would both decrease its cost and the chance for error and variation.

Brain waves, that is, oscillatory electrical brain activity, may be modeled as exponentially decaying sinusoid waveforms. This is based on the properties at the cell membrane level and the interactions of excitatory and inhibitory neurons.

Exponentially decaying sinusoid waveforms may be described by the parameters which define such waveforms. Those parameters are merely numbers, and thus are much easier to analyze than the complex graphs of the EEG. Further, the fact that the parameters are numbers allows the analysis itself to be automated.

Objects of the present invention are therefore to provide.

a. apparatus that applies to automated spike detection related to the analysis of EEG, evoked potentials, and related waveforms;

b. apparatus that does not require the compromising of data at the beginning or end of the data set;

c. apparatus that utilizes clustering in a two dimensional space;

d. apparatus that utilizes operations that are less subjective and less cumbersome than previous operations;

e. apparatus that calculates parameters related to the input waveform;

f. apparatus that lessens user interaction.

SUMMARY OF THE INVENTION

The present invention involves sampling the brain waves at regular intervals. Since different brain waves occur in different frequency bands, the sampling period is varied according to which brain wave is to be analyzed. The data obtained is manipulated in order to obtain an output comprising certain parameters. The parameters obtained from a particular patient are compared with standards for normal and abnormal brain waves to determine the condition which corresponds to the patient's brain waves. The standards comprise previously calculated parameters from a substantial number of patients whose brain waves are known to be normal and from a substantial number patients whose brain waves are known to be abnormal as a result of a variety of abnormal conditions. Thus, there are standards for the brain wave parameters for the normal condition and for the brain wave parameters for each of a variety of abnormal conditions.

The parameters calculated in the present invention are the Decay Parameter, the Wavelength Parameter, the Amplitude Parameter, the Phase Angles Parameter, and the Dwell Angle Parameter. Two means for calculating the Wavelength Parameter and the Dwell Angle Parameter are illustrated.

BRIEF DESCRIPTION OF THE DRAWINGS

FIGS. 4A and 4B are block diagrams of a means for calculating the Phase Angle Parameter according to the present invention;

DETAILED DESCRIPTION OF THE INVENTION

Figure 1:
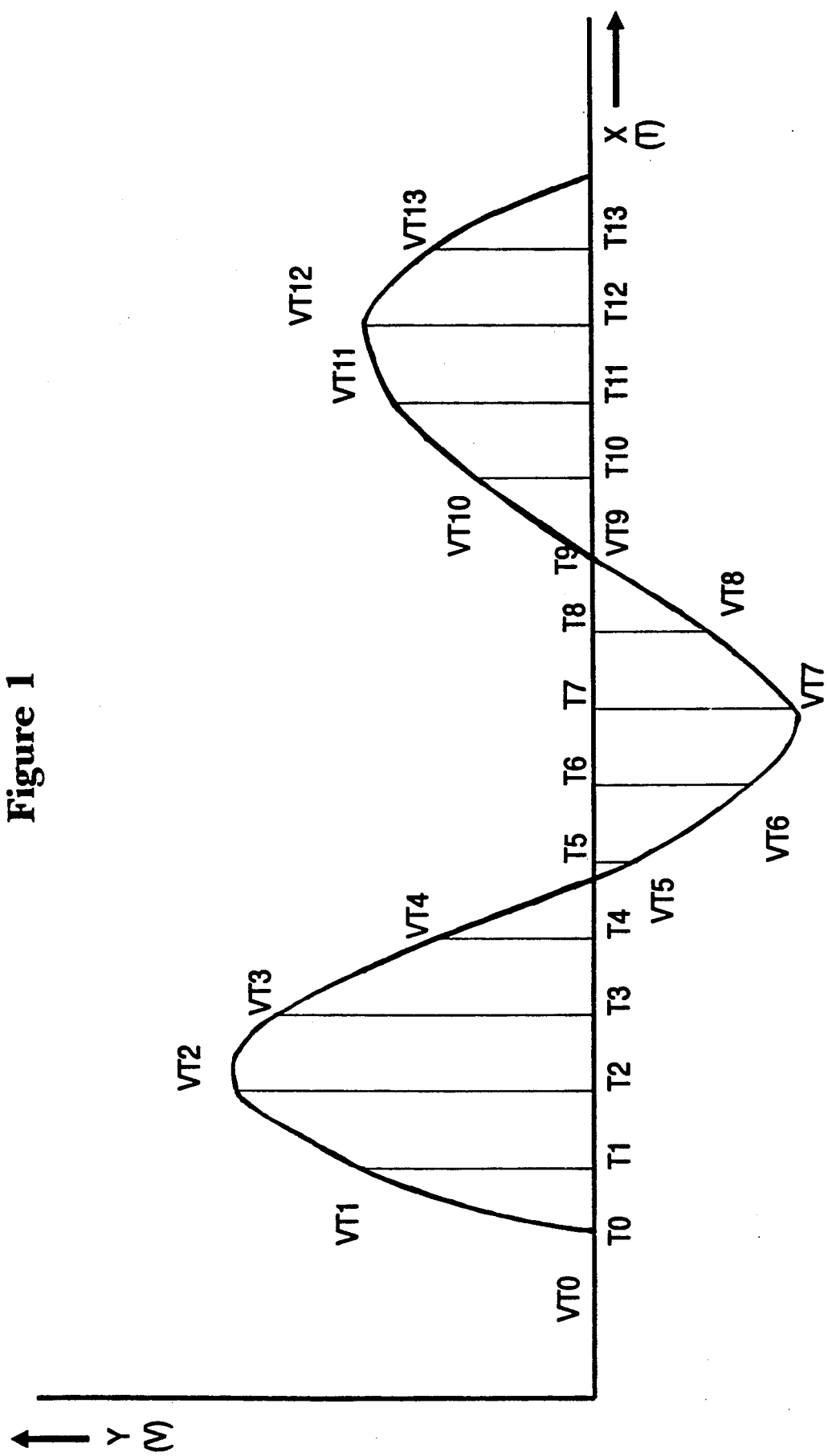
FIG. 1 is a diagram of a sample waveform to be analyzed.

FIG. 1 illustrates a sample input waveform from which the defined parameters are calculated. The waveform is plotted on the X and Y axes, where the X axis represents time T and the Y axis represents voltage V. As can be seen, the waveform is a sinusoid that decays at an exponential rate.

The input waveform amplitude is sampled at equal dwell time intervals; that is, time interval $=T1-T0=T2-T1$, and so on. The input waveform amplitude is $V_{T0}$ at time T0, $V_{T1}$ at time T1, $V_{T2}$ at time T2, $V_{Tn}$ at time Tn, and so forth.

Figure 2:
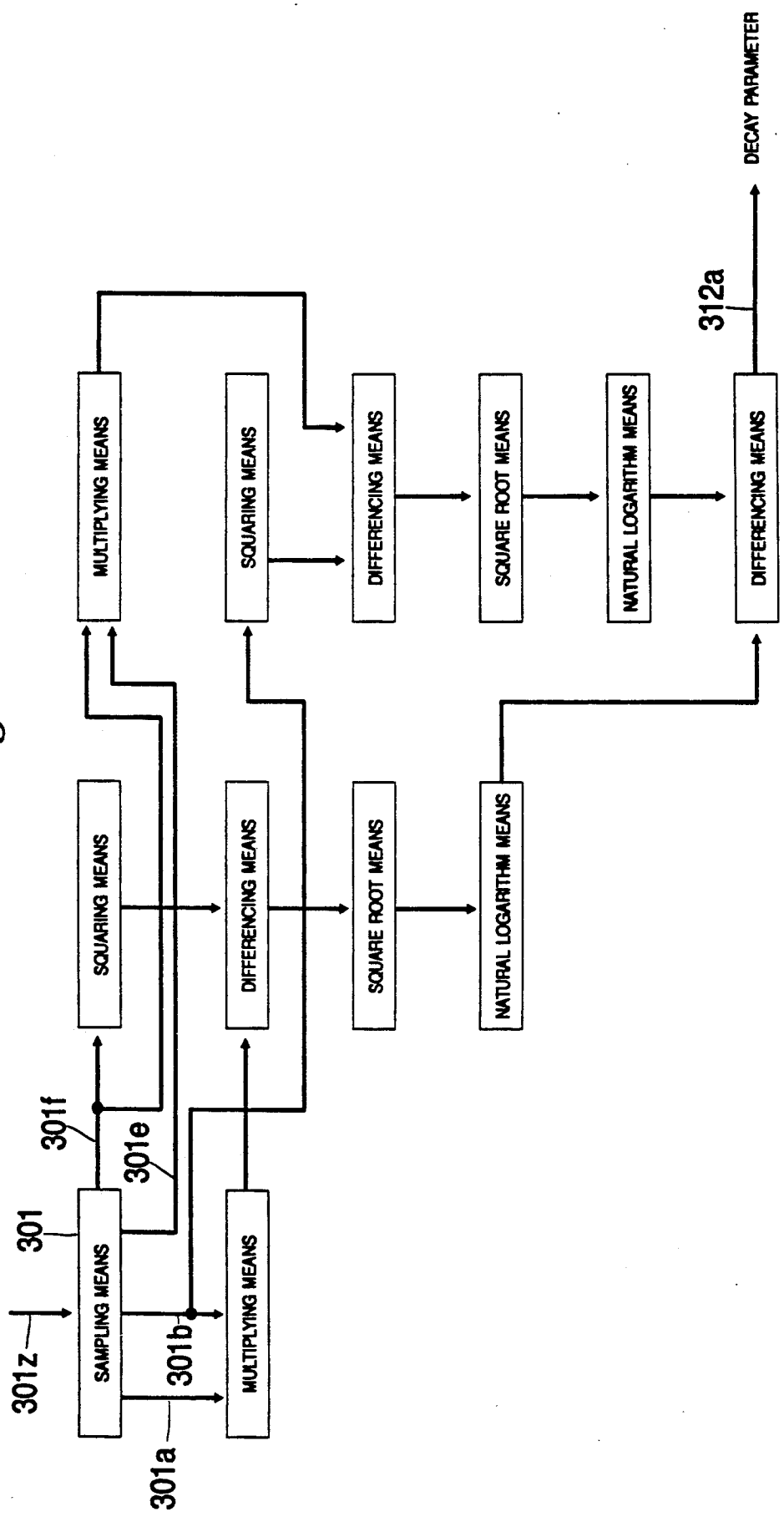
FIG. 2 is a block diagram of a means for calculating the Decay Parameter according to the present invention.

FIG. 2 illustrates a means for calculating and displaying and/or storing the Decay parameter. The input waveform is sampled by sampling means 301 at 300z. The outputs of sampling means 301 are: $V_{Tn}$ at 301a, $V_{Tn+1}$ at 301f, $V_{Tn+2}$ at 301b, and $V_{Tn+3}$ at 301e. The remaining means are interconnected as shown, resulting in the Decay Parameter at 312a. That The Decay Parameter calculated by the means shown in FIG. 2 is as follows:

$$\text{Decay Parameter} = \ln\sqrt{V_{Tn+1}^2 - V_{Tn} \times V_{Tn+2}} - \ln\sqrt{V_{Tn+2}^2 - V_{Tn+1} \times V_{Tn+3}}$$

Figure 3A:
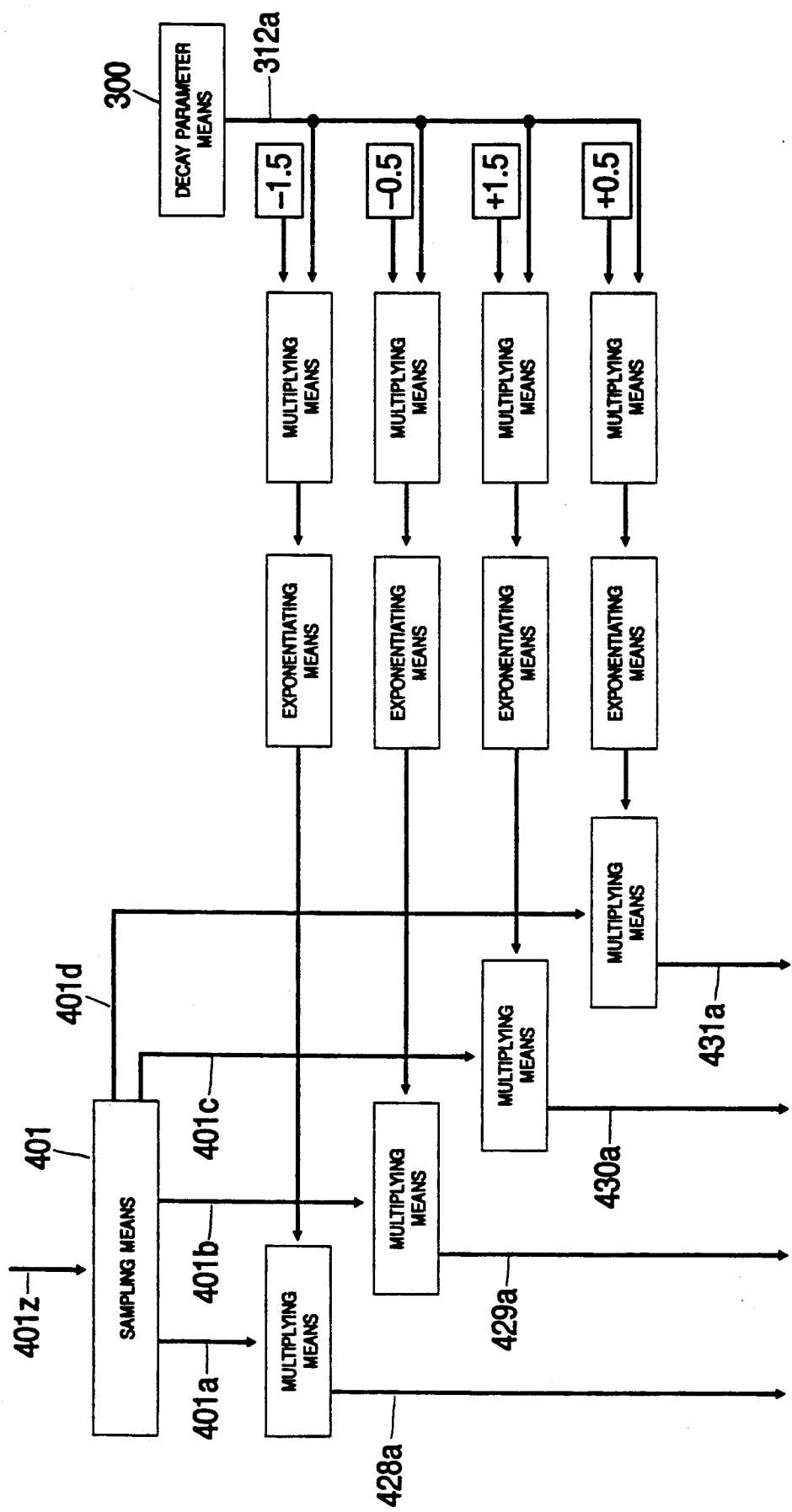
FIGS. 3A and 3B are block diagrams of a means for calculating the Amplitude Parameter, the Dwell Angle Parameter, and the Wavelength Parameter according to the present invention.
Figure 3B:
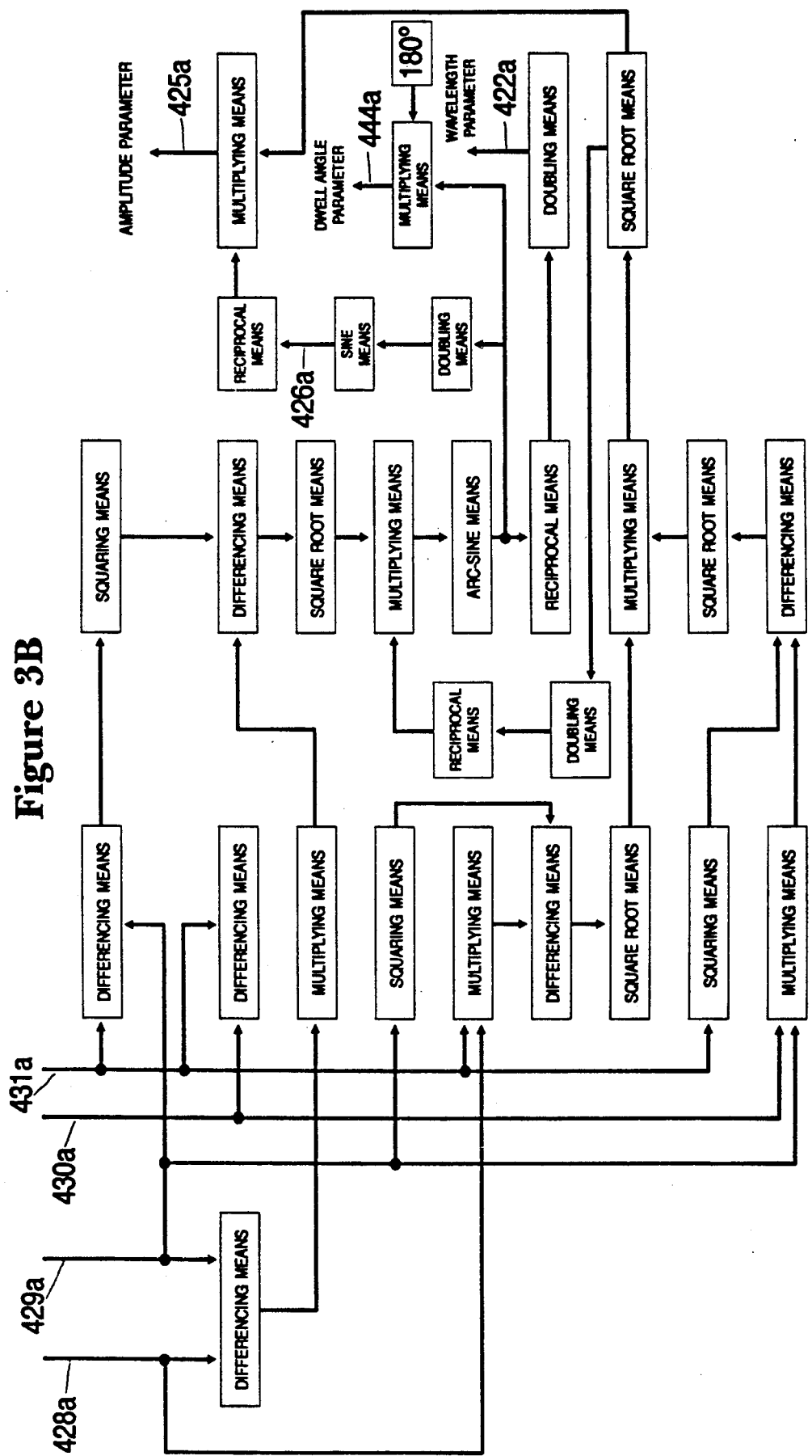

FIGS. 3A and 3B illustrate a means for calculating the Wavelength Parameter, the Amplitude Parameter, and the Dwell Angle Parameter.

In order to avoid unreliable results, it is necessary to normalize the input waveform samples. That is, the effect of the exponential decay is removed from the input waveform. That function is accomplished by the means illustrated in FIG. 3A.

The input waveform is sampled by sampling means 401 at 401z. The outputs of sampling means 401 are: $V_{Tn}$ at 401a, $V_{Tn+1}$ at 401b, $V_{Tn+2}$ at 401d, and $V_{Tn+3}$ at 401c. The Decay Parameter, as calculated by the means shown in FIG. 2, is inputted at 300a. The remaining means illustrated in FIG. 3A are interconnected as shown and result in the following normalized outputs: $V'_{Tn}$ at 428a, $V'_{Tn+1}$ at 429a, $V'_{Tn+2}$ at 431a, and $V'_{Tn+e}$ at 430a.

The outputs of FIG. 3A are the inputs to FIG. 3B. The remaining means in FIG. 3B are interconnected as shown, resulting in the Wavelength Parameter at 422a, the Amplitude Parameter at 425a, and the Dwell Angle Parameter at 444a.

The Wavelength Parameter, the Amplitude Parameter, and the Dwell Angle parameter calculated by the means in FIGS. 3A and 3B areas follows:

sampling means 501 are as follows: $V_{Tn}$ at 502a, $V_{Tn+1}$ at 501b, and $V_{Tn}$ at 502c. The normalized input waveform samples are as follows: $V'_{Tn+1}$ at 502a, $V'_{Tn+1}$ at 503a, and $V'_{Tn+2}$ at 504a. The remainder of the means in FIG. 4 are interconnected as shown, resulting in the calculation of the Phase Angle Parameter at 544a.

Figure 4A:
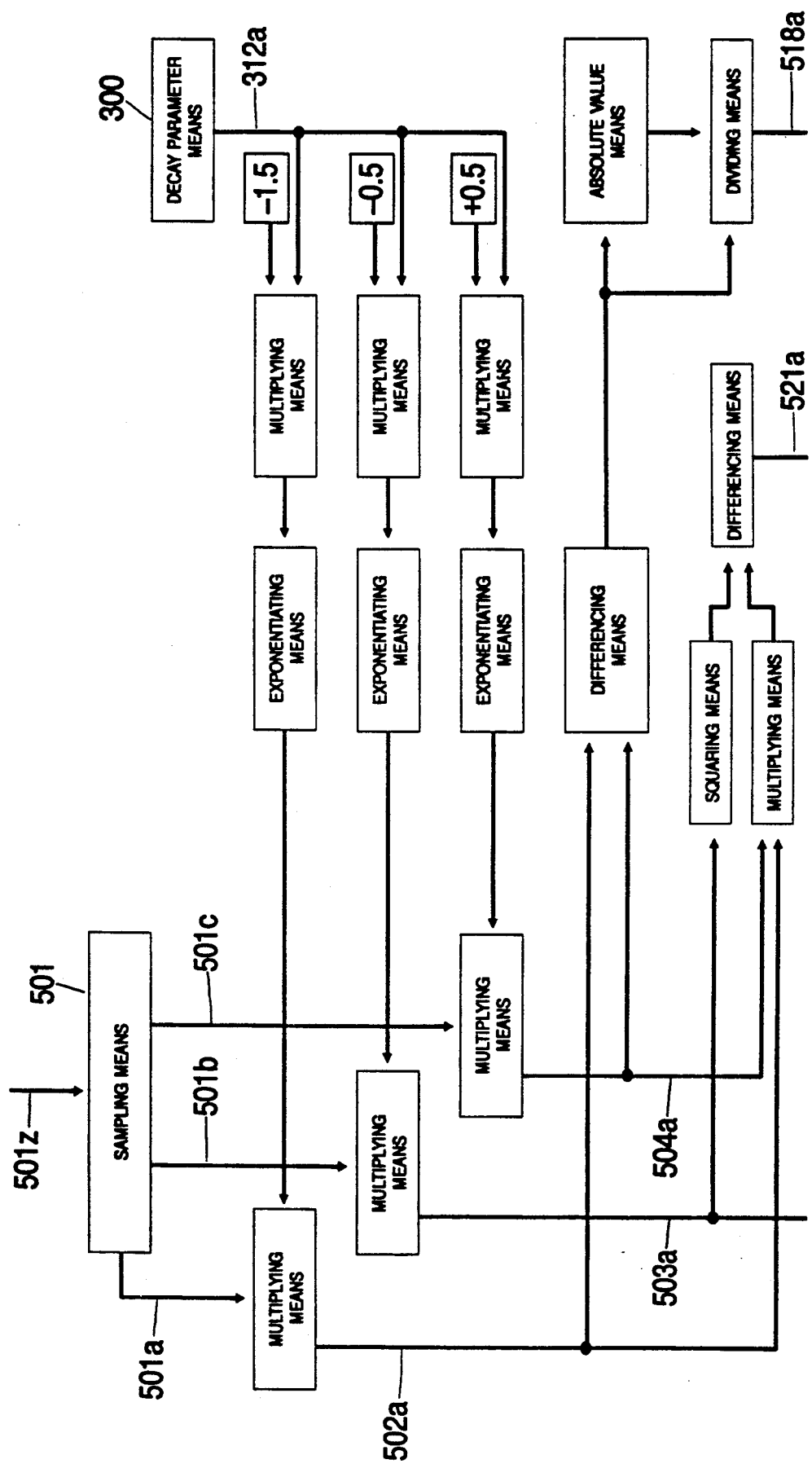

The Phase Angle Parameter as calculated by the means in FIGS. 4A and 4B is as follows:

$$\text{Phase Angle} = 90°\left[2 - \frac{\text{abs}\left(\sin\frac{V_{Tn+1}}{\text{Amp}}\right)}{\sin\frac{V_{Tn+1}}{\text{Amp}}} + \text{arccot}\frac{\frac{(-V_{Tn+1})}{\text{Amp}}}{\text{abs}\frac{(V_{Tn} - V_{Tn+2})}{V_{Tn} - V_{Tn+2}}\sqrt{1 - \left(\frac{V_{Tn+1}}{\text{Amp}}\right)^2}}\right],$$

when $V_{Tn+1} \neq 0$;

$$90°\left[1 - \frac{\text{abs}(V_{Tn} - V_{Tn+2})}{V_{Tn} - V_{Tn+2}}\right], \text{ when } V_{Tn+1} = 0,$$

Figure 5:
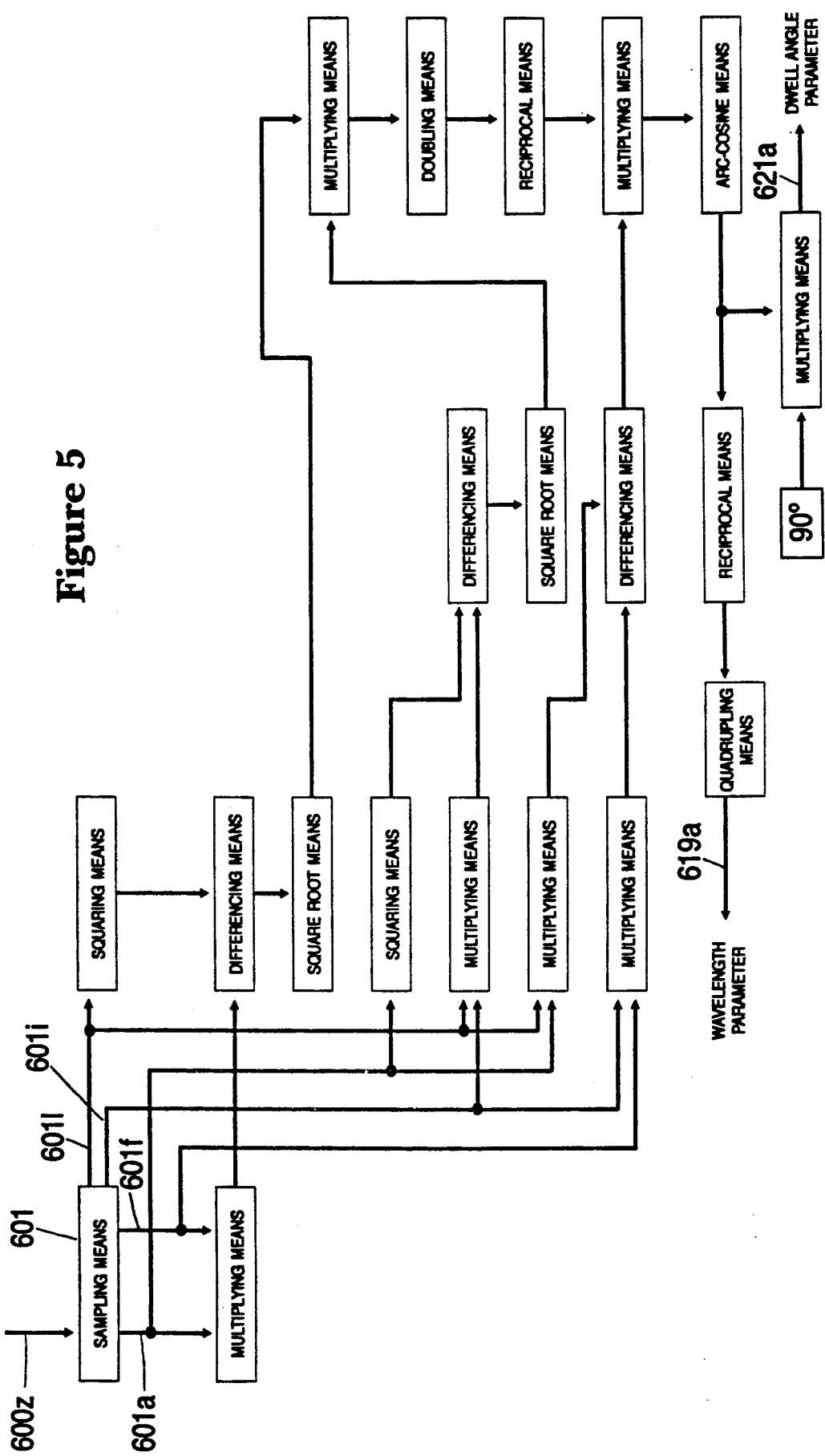
FIG. 5 is a block diagram of an alternate means for calculating the Wavelength Parameter and the Dwell Angle Parameter according to the present invention.

FIG. 5 illustrates an alternative means for calculating the Wavelength Parameter and the Dwell Angle Parameter.

The sampling means 601 samples the input waveform at 600z. The outputs of sampling means 601 are as follows: $V_{Tn}$ at 601i, $V_{Tn+1}$ at 601a, $V_{Tn+2}$ at 601l, and $V_{Tn+3}$ at 601f. The remainder of the means are interconnected as shown resulting in the Wavelength Parameter at 619a and the Dwell Angle Parameter at 621a.

$$\text{Wavelength Parameter} = \frac{2}{\arcsin\frac{\sqrt{(V_{Tn+1} - V_{Tn+2})^2 - (V_{Tn} - V_{Tn+1})(V_{Tn+2} - V_{Tn+3})}}{2\sqrt{\sqrt{V_{Tn+1}^{2'} - V_{Tn} \times V_{Tn+2}}\sqrt{V_{Tn+2}^{2'} - V_{Tn+1} \times V_{Tn+3}}}}};$$

$$\text{Amplitude Parameter} = \text{Amp} = \frac{\sqrt{V_{Tn+1}^{2'} - V_{Tn} \times V_{Tn+2}}}{\sin\left[2\arcsin\frac{\sqrt{(V_{Tn+1} - V_{Tn+2})^2 - (V_{Tn} - V_{Tn+1})(V_{Tn+2} - V_{Tn+3})}}{2\sqrt{\sqrt{V_{Tn+1}^{2'} - V_{Tn} \times V_{Tn+2}}\sqrt{V_{Tn+2}^{2'} - V_{Tn+1} \times V_{Tn+3}}}}\right]};$$

and $$\text{Dwell Angle Parameter} = 180°\left[\arcsin\frac{\sqrt{(V_{Tn+1} - V_{Tn+2})^2 - (V_{Tn} - V_{Tn+1})(V_{Tn+2} - V_{Tn+3})}}{2\sqrt{\sqrt{V_{Tn+1}^{2'} - V_{Tn} \times V_{Tn+2}}\sqrt{V_{Tn+2}^{2'} - V_{Tn+1} \times V_{Tn+3}}}}\right].$$

FIGS. 4A and 4B illustrate a means for calculating the Phase Angle Parameter.

Again, it is necessary to normalize the input waveform samples. The input waveform is sampled by sampling means 501 at 501z. The Decay Parameter, as determined in FIG. 2, is input at 312a. The outputs of The Wavelength Parameter and the Dwell Angle Parameter as calculated by the means in FIG. 5 are as follows:

$$\text{Wavelength Parameter} = \cfrac{4}{\arccos \cfrac{V_{Tn+1} \times V_{Tn+2} - V_{Tn} \times V_{Tn+3}}{2\sqrt{(V^2_{Tn+1} - V_{Tn} \times V_{Tn+2}) \times (V^2_{Tn+2} - V_{Tn+1} \times V_{Tn+3})}}};$$

$$\text{Dwell Angle Parameter} = 90° \left[ \arccos \cfrac{V_{Tn+1} \times V_{Tn+2} - V_{Tn} \times V_{Tn+3}}{2\sqrt{(V^2_{Tn+1} - V_{Tn} \times V_{Tn+2})(V^2_{Tn+2} - V_{Tn+1} \times V_{Tn+3})}} \right].$$

Figure 6:
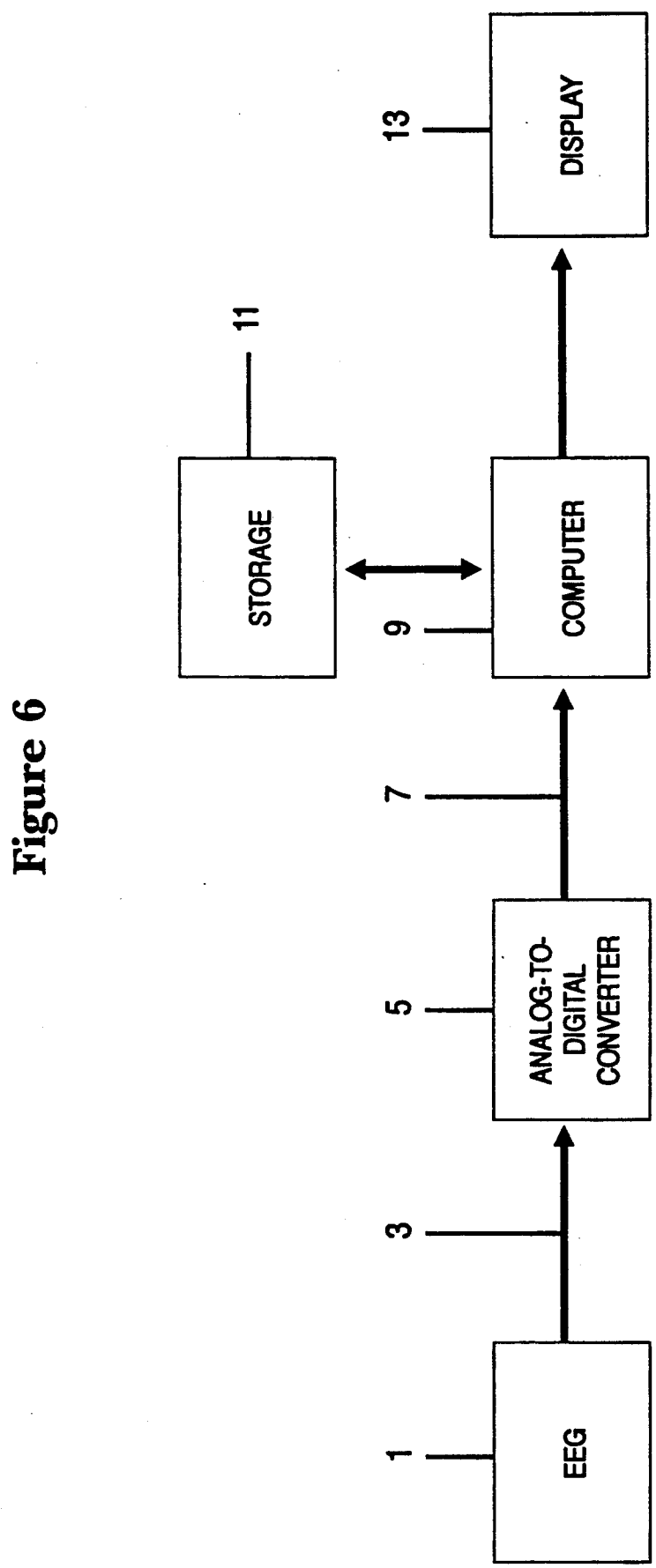
FIG. 6 is a block diagram of a preferred embodiment of the present invention.

FIG. 6 is a block diagram of a preferred embodiment of the present invention. A patient (not shown) is electrically connected to a conventional EEG 1. The electrical output 3 of the EEG 1 is digitalized by an analog-to-digital converter 5. The analog-to-digital converter output 7 is the input to a digital computer 9. The computer 9 is programmed to sample the EEG output 3 and calculate the decay, wavelength, amplitude, dwell angle, and phase angle parameters for the patient's brain waves.

Standards for the parameters for normal brain waves and for brain waves resulting from a variety of abnormal conditions are stored in a suitable nonvolatile storage means 11, such as a floppy disk or hard disk. The standards for normal brain waves are formulated by calculating the parameters of the brain waves of a substantial number of patients known to have normal brain waves. In like manner, the standards for brain waves for each abnormal condition are formulated by calculating the parameters for the brain waves of a substantial number of patients known to have that abnormal condition.

The computer 9 compares the patient's parameters with the standards for normal and abnormal brain waves contained in the storage means 11 to determine the condition corresponding to the patient's brain waves. That is, the comparison determines whether the patient's brain waves correspond to a normal condition or to one of a plurality of abnormal conditions. The result of the comparison is then displayed on a display 13.

In addition to the foregoing, the output of the analog-to-digital converter 5 is stored in the storage means 11 and, if desired, may be displayed on the display 13. This produces a display that is essentially identical to that of a conventional EEG, allowing a physician or technician to confirm the results of the computer analysis. The patient's calculated parameters are also stored in the storage means 11, allowing the analysis to be performed in the absence of the patient.

In an alternate embodiment of the invention, the parameters are calculated as described above and the comparison of the calculated parameters with the normal and abnormal standards is accomplished by the physician or technician.

I claim:

1. A method for analyzing the brain waves of a patient comprising the steps of:
    sampling said brain waves periodically, the sampling period being variable in order to detect the particular brain waves of interest;
    calculating parameters which describe said brain waves;
    comparing said calculated parameters with standards for said parameters for normal and a plurality of abnormal brain waves to determine the condition which corresponds to the patient's brain waves; and
    displaying the result of said comparison.

2. The method for of claim 1 wherein said brain wave samples are sequentially designated $V_{Tn}$, $V_{Tn+1}$, $V_{Tn+2}$ and $V_{Tn+3}$, wherein said brain wave samples are normalized to remove the effect of an exponential decay of said brain waves, said normalized brain wave samples being designated $V'_{Tn}$, $V'_{Tn+2}$, and $V'_{Tn+3}$, and wherein the parameters that described the patient's brain waves comprise:

$$\text{Decay Parameter} = \ln\sqrt{V^2_{Tn+1} - V_{Tn} \times V_{Tn+2}} - \ln\sqrt{V^2_{Tn+2} - V_{Tn+1} \times V_{Tn+3}};$$

$$\text{Wavelength Parameter} = \cfrac{2}{\arcsin \cfrac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V'^2_{Tn+1} - V'_{Tn} \times V'_{Tn+2}}\sqrt{V'^2_{Tn+2} - V'_{Tn+1} \times V'_{Tn+3}}}}};$$

$$\text{Amplitude Parameter} = \text{Amp} = \cfrac{\sqrt{V'^2_{Tn+1} - V'_{Tn} \times V'_{Tn+2}}}{\sin\left[2\arcsin \cfrac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V'^2_{Tn+1} - V'_{Tn} \times V'_{Tn+2}}\sqrt{V'^2_{Tn+2} - V'_{Tn+1} \times V'_{Tn+3}}}}\right]};$$

-continued $$\text{Phase Angle Parameter} = 90° \left[ 2 - \frac{\text{abs}\left(\sin\frac{V_{Tn+1}}{Amp}\right)}{\sin\frac{V_{Tn+1}}{Amp}} + \text{arccot} \frac{\frac{(-V_{Tn+1})}{Amp}}{\frac{\text{abs}(V_{Tn} - V_{tn+2})}{V_{Tn} - V_{Tn+2}}\sqrt{1 - \left(\frac{V_{Tn+1}}{Amp}\right)^2}} \right],$$

when $V_{Tn+1} \neq 0$;

$$90° \left[ 1 - \frac{\text{abs}(V_{Tn} - V_{Tn+2})}{V_{Tn} - V_{Tn+2}} \right], \text{ when } V_{Tn+1} = 0;$$

and $$\text{Dwell Angle Parameter} = 180° \left[ \arcsin \frac{\sqrt{(V_{Tn+1} - V_{Tn+2})^2 - (V_{Tn} - V_{Tn+1})(V_{Tn+2} - V_{Tn+3})}}{2\sqrt{\sqrt{V_{Tn+1}^{2'} - V_{Tn} \times V_{Tn+2}}\sqrt{V_{Tn+2}^{2'} - V_{Tn+1} \times V_{Tn+3}}}} \right].$$

3. The method of claim 2 wherein:

$$\text{Wavelength Parameter} = \frac{4}{\arccos \frac{V_{Tn+1} \times V_{Tn+2} - V_{Tn} \times V_{Tn+3}}{2\sqrt{(V_{Tn+1}^2 - V_{Tn} \times V_{Tn+2}) \times (V_{Tn+2}^2 - V_{Tn+1} \times V_{Tn+3}]}}};$$

$$\text{Dwell Angle Parameter} = 90° \left[ \arccos \frac{V_{Tn+1} \times V_{Tn+2} - V_{Tn} \times V_{Tn+3}}{2\sqrt{(V_{Tn+1}^2 - V_{Tn} \times V_{Tn+2})(V_{Tn+2}^2 - V_{Tn+1} \times V_{Tn+3})}} \right].$$

4. The method of claim 1 further comprising storing said brain wave samples and said calculated parameters to allow analysis of said brain wave samples and said parameters in the absence of the patient.

5. An apparatus for analyzing the brain waves of a patient comprising:
 means for sampling said brain waves periodically, the sampling period being variable in order to detect the particular brain waves of interest;
 means for calculating parameters which describe said brain waves;
 means for comparing said calculated parameters with standards for said parameters for normal and a plurality of abnormal brain waves to determine the condition corresponding to the patient's brain waves to and
 means for displaying the result of said comparison.

6. The apparatus of claim 5 wherein said brain wave samples are sequentially designated $V_{Tn}$, $V_{Tn+1}$, $V_{Tn+2}$ and $V_{Tn+3}$, wherein said brain wave samples are normalized to remove the effect of an exponential decay of brain waves, said normalized brain wave samples being designated $V'_{Tn}$, $V'_{TN+1}$, $V'_{Tn+2}$, and $V'_{Tn+3}$, and wherein the parameters that describe brain waves comprise:

$$\text{Decay Parameter} = \ln\sqrt{V_{Tn+1}^2 - V_{Tn} \times V_{Tn+2}} - \ln\sqrt{V_{Tn+2}^2 - V_{Tn+1} \times V_{Tn+3}};$$

$$\text{Wavelength Parameter} = \frac{2}{\arcsin \frac{\sqrt{(V_{Tn+1} - V_{Tn+2})^2 - (V_{Tn} - V_{Tn+1})(V_{Tn+2} - V_{Tn+3})}}{2\sqrt{\sqrt{V_{Tn+1}^{2'} - V_{Tn} \times V_{Tn+2}}\sqrt{V_{Tn+2}^{2'} - V_{Tn+1} \times V_{Tn+3}}}}};$$

$$\text{Amplitude Parameter} = Amp = \frac{\sqrt{V_{Tn+1}^{2'} - V_{Tn} \times V_{Tn+2}}}{\sin\left[2\arcsin\frac{\sqrt{(V_{Tn+1} - V_{Tn+2})^2 - (V_{Tn} - V_{Tn+1})(V_{Tn+2} - V_{Tn+3})}}{2\sqrt{\sqrt{V_{Tn+1}^{2'} - V_{Tn} \times V_{Tn+2}}\sqrt{V_{Tn+2}^{2'} - V_{Tn+1} \times V_{Tn+3}}}}\right]};$$

$$\text{Phase Angle Parameter} = 90° \left[ 2 - \frac{\text{abs}\left(\sin \frac{V_{Tn+1}}{\text{Amp}}\right)}{\sin \frac{V_{Tn+1}}{\text{Amp}}} + \text{arccot} \frac{\frac{(-V_{Tn+1})}{\text{Amp}}}{\frac{\text{abs}(V_{Tn} - V_{Tn+2})}{V_{Tn} - V_{Tn+2}} \sqrt{1 - \left(\frac{V_{Tn+1}}{\text{Amp}}\right)^2}} \right],$$

when $V_{Tn+1} \neq 0$;

$$90° \left[ 1 - \frac{\text{abs}(V_{Tn} - V_{Tn+2})}{V_{Tn} - V_{Tn+2}} \right], \text{ when } V_{Tn+1} = 0;$$

and $$\text{Dwell Angle Parameter} = 180° \left[ \arcsin \frac{\sqrt{(V_{Tn+1} - V_{Tn+2})^2 - (V_{Tn} - V_{Tn+1})(V_{Tn+2} - V_{Tn+3})}}{2 \sqrt{\sqrt{V^2_{Tn+1} - V_{Tn} \times V_{Tn+2}} \sqrt{V^2_{Tn+2} - V_{Tn+1} \times V_{Tn+3}}} } \right].$$

7. The apparatus of claim 6 wherein:

$$\text{Wavelength Parameter} = \frac{4}{\arccos \frac{V_{Tn+1} \times V_{Tn+2} - V_{Tn} \times V_{Tn+3}}{2 \sqrt{(V^2_{Tn+1} - V_{Tn} \times V_{Tn+2}) \times (V^2_{Tn+2} - V_{Tn+1} \times V_{Tn+3})}}};$$

$$\text{Dwell Angle Parameter} = 90° \left[ \arccos \frac{V_{Tn+1} \times V_{Tn+2} - V_{Tn} \times V_{Tn+3}}{2 \sqrt{(V^2_{Tn+1} - V_{Tn} \times V_{Tn+2})(V^2_{Tn+2} - V_{Tn+1} \times V_{Tn+3})}} \right].$$

8. The apparatus of claim 5 further comprising means for storing said brain wave samples and said calculated parameters to allow analysis of said samples and said parameters in the absence of the patient.

* * * * *

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

IN THE DRAWINGS

In Fig. 3B, insert an arrow from the DIFFERENCING MEANS block having inputs 430a and 431b to the MULTIPLYING MEANS block immediately below said DIFFERENCING MEANS block.

In Fig. 4B, delete the arrow from the MULTIPLYING MEANS block having input 518a to the ARC-COTANGENT MEANS block and insert an arrow from said MULTIPLYING MEANS block to the MULTIPLYING MEANS block immediately above said ARC-COTANGENT MEANS block.

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

At column 1, line 8, change "relating" to -- related --.

At column 1, line 36, center "INTRODUCTION".

At column 1, line 57, change "." to -- : --.

At column 2, beginning on line 62, delete "and displayin and/or storing".

At column 2, line 66, change "$V_{Tn}+1$" to -- $V_{Tn+1}$ --, chang "$V_{Tn}+2$" to -- $V_{Tn+2}$ --, and change "$V_{Tn}+3$" to -- $V_{Tn+3}$ --.

At column 2, line 68, delete "That".

At column 3, line 28, change "$V'_{Tn+e}$" to -- $V'_{Tn+3}$ --.

At column 4, line 1, change "502a" to -- 501a --.

At column 4, line 2, change "$V_{Tn}$ at 502c" to -- $V_{Tn+2}$ at 501c --.

At column 4, line 3, change "$V'_{Tn+1}$" to -- $V'_{Tn}$ --.

UNITED STATES PATENT AND TRADEMARK OFFICE
CERTIFICATE OF CORRECTION

PATENT NO. : 5,195,530  
DATED : March 23, 1993  
INVENTOR(S) : Larry Shindel

Page 3 of 15

It is certified that error appears in the above-indentified patent and that said Letters Patent is hereby corrected as shown below:

At column 4, in the equation for "Phase Angle" beginning a line 10, change "

$$\text{arccot} \frac{(-V'_{Tn+1})/Amp}{\text{abs}\frac{(V'_{Tn} - V'_{Tn+2})}{V'_{Tn} - V'_{Tn+2}} \sqrt{1 - \left(\frac{V'_{Tn+1}}{Amp}\right)^2}}$$

" to --

$$\text{arccot} \frac{(-V'_{Tn+1})/Amp}{\frac{\text{abs}(V'_{Tn} - V'_{Tn+2})}{V'_{Tn} - V'_{Tn+2}} \sqrt{1 - \left(\frac{V'_{Tn+1}}{Amp}\right)^2}}$$

--. As corrected, tl

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

equation for "Phase Angle" reads as follows:

$$90° \left[ 2 - \frac{abs(\sin \frac{V'_{Tn+1}}{Amp})}{\sin \frac{V'_{Tn+1}}{Amp}} + \text{arccot} \frac{(-V'_{Tn+1})/Amp}{\frac{abs(V'_{Tn} - V'_{tn+2})}{V'_{Tn} - V'_{Tn+2}} \sqrt{1 - (\frac{V'_{Tn+1}}{Amp})^2}} \right],$$

when $V'_{Tn+1} \neq 0$;

$$90° \left[ 1 - \frac{abs(V'_{Tn} - V'_{Tn+2})}{V'_{Tn} - V'_{Tn+2}} \right], \text{ when } V'_{Tn+1} = 0;$$

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

At column 5, in the denominator of the equation for "Dwell Angle Parameter", please change "$V'_{Tn}$" to -- $VTn$ --. As corrected the equation for "Dwell Angle Parameter" reads as follows:

$$90°[\arccos \frac{V_{Tn+1} \times V_{Tn+2} - V_{Tn} \times V_{Tn+3}}{2\sqrt{(V^2_{Tn+1} - V_{Tn} \times V_{Tn+2})(V^2_{Tn+2} - V_{Tn+1} \times V_{Tn+3})}}).$$

Column 6:
In claim 2, line 44, please insert -- $V'_{Tn+1}$ -- between "$V'_{Tn}$" and "$V'_{Tn+2}$". As corrected, claim 2 reads as follows:

2. The method of Claim 1 wherein said brain wave samples are sequentially designated $V_{Tn}$, $V_{Tn+1}$, $V_{Tn+2}$ and $V_{Tn+3}$, wherein said brain wave samples are normalized to remove the effect of an exponential decay of said brain waves, said normalized brain wave samples being

UNITED STATES PATENT AND TRADEMARK OFFICE
CERTIFICATE OF CORRECTION

PATENT NO. : 5,195,530  
DATED : March 23, 1993  
INVENTOR(S) : Larry Shindel

Page 6 of 15

It is certified that error appears in the above-indentified patent and that said Letters Patent is hereby corrected as shown below:

designated $V'_{Tn}$, $V'_{Tn+1}$, $V'_{Tn+2}$, and $V'_{Tn+3}$, , and wherein the parameter that describe the patient's brain waves comprise:

Decay Parameter =

$$\ln \sqrt{V_{Tn+1}^2 - V_{Tn} \times V_{Tn+2}} - \ln \sqrt{V_{Tn+2}^2 - V_{Tn+1} \times V_{Tn+3}};$$

Wavelength Parameter =

$$\frac{2}{\arcsin \frac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V_{Tn+1}^{2'} - V'_{Tn} \times V'_{Tn+2}} \sqrt{V_{Tn+2}^{2'} - V'_{Tn+1} \times V'_{Tn+3}}}}};$$

Amplitude Parameter = Amp =

$$\frac{\sqrt{V_{Tn+1}^{2'} - V'_{Tn} \times V'_{Tn+2}}}{\sin \left[ 2\arcsin \frac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V_{Tn+1}^{2'} - V'_{Tn} \times V'_{Tn+2}} \sqrt{V_{Tn+2}^{2'} - V'_{Tn+1} \times V'_{Tn+3}}}} \right]};$$

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

Phase Angle Parameter=

$$90° \left[2 - \frac{abs\left(\sin \frac{V'_{Tn+1}}{Amp}\right)}{\sin \frac{V'_{Tn+1}}{Amp}} + \text{arccot} \frac{\frac{(-V'_{Tn+1})}{Amp}}{\frac{abs(V'_{Tn} - V'_{tn+2})}{V'_{Tn} - V'_{Tn+2}} \sqrt{1 - \left(\frac{V'_{Tn+1}}{Amp}\right)^2}}\right],$$

$$\text{when } V'_{Tn+1} \neq 0;$$

$$90° \left[1 - \frac{abs(V'_{Tn} - V'_{Tn+2})}{V'_{Tn} - V'_{Tn+2}}\right], \text{ when } V'_{Tn+1} = 0;$$

and

Dwell Angle Parameter =

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

$$180° [\arcsin \frac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V_{Tn+1}^{2'} - V'_{Tn} \times V'_{Tn+2}} \sqrt{V_{Tn+2}^{2'} - V'_{Tn+1} \times V'_{Tn+3}}}}].$$

Column 7:
In claim 3, 1st line, delete "means for comparing sai calculated parameters with". As corrected, claim 3 reads a follows:

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

3. The method of claim 2 wherein:

Wavelength Parameter =

$$\frac{4}{\arccos \dfrac{V_{Tn+1} \times V_{Tn+2} - V_{Tn} \times V_{Tn+3}}{2\sqrt{(V_{Tn+1}^2 - V_{Tn} \times V_{Tn+2}) \times (V_{Tn+2}^2 - V_{Tn+1} \times V_{Tn+3})}]}};$$

Dwell Angle Parameter =

$$90^\circ [\arccos \frac{V_{Tn+1} \times V_{Tn+2} - V_{Tn} \times V_{Tn+3}}{2\sqrt{(V_{Tn+1}^2 - V_{Tn} \times V_{Tn+2})(V_{Tn+2}^2 - V_{Tn+1} \times V_{Tn+3})}}).$$

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

In claim 5, following the 7th line, insert -- means fo comparing said calculated parameters with --.

In claim 5, 11th line, change "to" to -- ; --.

As corrected by the foregoing two corrections, claim 5 read as follows:

5. An apparatus for analyzing the brain waves of a patien comprising:

means for sampling said brain waves periodically, the samplin period being variable in order to detect the particular brain wave of interest;

means for calculating parameters which describe said brai waves;

means for comparing said calculated parameters with standard for said parameters for normal and a plurality of abnormal brai waves to determine the condition corresponding to the patient' brain waves; and means for displaying the result of said comparison.

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

In claim 6, 5th line, insert -- said -- between "of" and "brain".

In claim 6, 6th line, change "$V'_{TN+1}$" to -- $V'_{Tn+1}$ --.

As corrected by the foregoing two corrections, claim 6 reads as follows:

6. The apparatus of Claim 5 wherein said brain wave samples are sequentially designated $V_{Tn}$, $V_{Tn+1}$, $V_{Tn+2}$ and $V_{Tn+3}$, wherein said brain wave samples are normalized to remove the effect of a exponential decay of said brain waves, said normalized brain wave samples being designated $V'_{Tn}$, $V'_{Tn+1}$, $V'_{Tn+2}$, and $V'_{Tn+3}$, , and wherein the parameters that describe brain waves comprise:

Decay Parameter = $\ln \sqrt{V^2_{Tn+1} - V_{Tn} \times V_{Tn+2}} - \ln \sqrt{V^2_{Tn+2} - V_{Tn+1} \times V_{Tn+3}}$;

UNITED STATES PATENT AND TRADEMARK OFFICE
CERTIFICATE OF CORRECTION

PATENT NO. : 5,195,530

DATED : March 23, 1993

INVENTOR(S) : Larry Shindel

It is certified that error appears in the above-indentified patent and that said Letters Patent is hereby corrected as shown below:

Wavelength Parameter =

$$\frac{2}{\arcsin \frac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V'^2_{Tn+1} - V'_{Tn} \times V'_{Tn+2}} \sqrt{V'^2_{Tn+2} - V'_{Tn+1} \times V'_{Tn+3}}}}};$$

Amplitude Parameter = Amp =

$$\frac{\sqrt{V'^2_{Tn+1} - V'_{Tn} \times V'_{Tn+2}}}{\sin\left[2\arcsin \frac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V'^2_{Tn+1} - V'_{Tn} \times V'_{Tn+2}} \sqrt{V'^2_{Tn+2} - V'_{Tn+1} \times V'_{Tn+3}}}}\right]};$$

UNITED STATES PATENT AND TRADEMARK OFFICE
CERTIFICATE OF CORRECTION

PATENT NO. : 5,195,530  
DATED : March 23, 1993  
INVENTOR(S) : Larry Shindel

Page 13 of 15

It is certified that error appears in the above-indentified patent and that said Letters Patent is hereby corrected as shown below:

Phase Angle Parameter=

$$90° \left[ 2 - \frac{abs(\sin \frac{V'_{Tn+1}}{Amp})}{\sin \frac{V'_{Tn+1}}{Amp}} + \text{arccot} \frac{\frac{(-V'_{Tn+1})}{Amp}}{\frac{abs(V'_{Tn} - V'_{tn+2})}{V'_{Tn} - V'_{Tn+2}} \sqrt{1 - \left(\frac{V'_{Tn+1}}{Amp}\right)^2}} \right],$$

when $V'_{Tn+1} \neq 0$;

$$90° \left[ 1 - \frac{abs(V'_{Tn} - V'_{Tn+2})}{V'_{Tn} - V'_{Tn+2}} \right], \text{ when } V'_{Tn+1} = 0;$$

and

Dwell Angle Parameter =

$$180° \left[ \arcsin \frac{\sqrt{(V'_{Tn+1} - V'_{Tn+2})^2 - (V'_{Tn} - V'_{Tn+1})(V'_{Tn+2} - V'_{Tn+3})}}{2\sqrt{\sqrt{V'^{2}_{Tn+1} - V'_{Tn} \times V'_{Tn+2}} \sqrt{V'^{2}_{Tn+2} - V'_{Tn+1} \times V'_{Tn+3}}} } \right].$$

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

In claim 7, 1st line, delete "parameters to allow analysis of said samples and said". As corrected, claim 7 reads as follows:

7. The apparatus of claim 6 wherein:

Wavelength Parameter =

$$\frac{4}{\arccos \frac{V_{Tn+1} \times V_{Tn+2} - V_{Tn} \times V_{Tn+3}}{2\sqrt{(V_{Tn+1}^2 - V_{Tn} \times V_{Tn+2}) \times (V_{Tn+2}^2 - V_{Tn+1} \times V_{Tn+3}]}}};$$

Dwell Angle Parameter =

$$90° [\arccos \frac{V_{Tn+1} \times V_{Tn+2} - V_{Tn} \times V_{Tn+3}}{2\sqrt{(V_{Tn+1}^2 - V_{Tn} \times V_{Tn+2})(V_{Tn+2}^2 - V_{Tn+1} \times V_{Tn+3})}}).$$

UNITED STATES PATENT AND TRADEMARK OFFICE
CERTIFICATE OF CORRECTION

PATENT NO. : 5,195,530
DATED : March 23, 1993
INVENTOR(S) : Larry Shindel

It is certified that error appears in the above-indentified patent and that said Letters Patent is hereby corrected as shown below:

In claim 8, following the 2d line, insert -- paramaters to allow analysis of said samples and said --. As corrected, claim 8 reads as follows:

8. The apparatus of claim 5 further comprising means for storing said brain wave samples and said calculated parameters to allow analysis of said samples and said parameters in the absence of the patient.

Signed and Sealed this

Second Day of August, 1994

*Attest:*

BRUCE LEHMAN

*Attesting Officer*     *Commissioner of Patents and Trademarks*